(12) United States Patent  (10) Patent No.: US 7,097,070 B2
Massaro et al.  (45) Date of Patent: Aug. 29, 2006

(54) METHOD AND APPARATUS FOR HANDLING SMALL VOLUME FLUID SAMPLES

(75) Inventors: Peter Massaro, Burlington, CT (US); Benjamin F. Geldhof, East Hartford, CT (US)

(73) Assignee: Protedyne Corporation, Windsor, CT (US)

( * ) Notice: Subject to any disclaimer, the term of this patent is extended or adjusted under 35 U.S.C. 154(b) by 207 days.

(21) Appl. No.: 10/641,523

(22) Filed: Aug. 15, 2003

(65) Prior Publication Data

US 2005/0035143 A1  Feb. 17, 2005

(51) Int. Cl.
B67D 5/42 (2006.01)
(52) U.S. Cl. ........................ 222/1; 222/386.5
(58) Field of Classification Search .................. 222/1
See application file for complete search history.

(56) References Cited

U.S. PATENT DOCUMENTS

| | | |
|---|---|---|
| 2,264,564 A | 12/1941 | Conner |
| 3,575,220 A | 4/1971 | Davis et al. |
| 4,042,152 A | 8/1977 | Drbal |
| 4,058,367 A | 11/1977 | Gilford |
| 4,083,690 A | 4/1978 | Inoue |
| 4,152,390 A | 5/1979 | Nosco et al. |
| 4,311,484 A | 1/1982 | Fosslien |
| 4,323,537 A | 4/1982 | Mody |
| 4,325,910 A | 4/1982 | Jordan |
| 4,351,799 A | 9/1982 | Gross et al. |
| 4,352,780 A | 10/1982 | Schick |
| 4,436,822 A | 3/1984 | Eseifan |
| 4,454,095 A | 6/1984 | Holt |
| 4,482,345 A | 11/1984 | Chow et al. |
| 4,503,012 A | 3/1985 | Starr |
| 4,517,160 A | 5/1985 | Galle et al. |
| 4,558,946 A | 12/1985 | Galle et al. |
| 4,597,412 A | 7/1986 | Stark |
| 4,673,657 A | 6/1987 | Christian |
| 4,681,741 A | 7/1987 | Hanaway |
| 4,695,430 A | 9/1987 | Coville et al. |
| 4,774,055 A | 9/1988 | Wakatake et al. |
| 4,781,891 A | 11/1988 | Galle et al. |
| 4,844,872 A | 7/1989 | Geiselman et al. |
| 4,863,066 A * | 9/1989 | Uffenheimer et al. .......... 222/1 |
| 4,876,204 A | 10/1989 | Inoue et al. |
| 4,906,432 A | 3/1990 | Geiselman |
| 4,965,049 A | 10/1990 | Lillig et al. |
| 4,980,130 A | 12/1990 | Metzger et al. |

(Continued)

FOREIGN PATENT DOCUMENTS

DE  19737173 A1  3/1999

(Continued)

OTHER PUBLICATIONS

International Search Report PCT/US2004/026453 dated Nov. 30, 2004.

*Primary Examiner*—J. Casimer Jacyna
(74) *Attorney, Agent, or Firm*—Wolf, Greenfield & Sacks, P.C.

(57) ABSTRACT

A small-volume sample handling system includes a chamber with first and second portions. A conduit having a flow control valve may be fluidly coupled to the first portion. A pressure in the second portion may be adjusted so that liquid samples can be aspirated and dispensed in a needle coupled to the valve in response to opening of the valve. The first and second portions of the chamber may be separated by a diaphragm.

21 Claims, 2 Drawing Sheets

U.S. PATENT DOCUMENTS

| | | | |
|---|---|---|---|
| 4,988,482 A | 1/1991 | Weston | |
| 5,012,845 A | 5/1991 | Averette | |
| 5,019,348 A | 5/1991 | Ohms et al. | |
| 5,037,611 A | 8/1991 | Ledford, Jr. | |
| 5,047,129 A | 9/1991 | Nardo | |
| 5,049,359 A | 9/1991 | Azuma et al. | |
| 5,056,462 A | 10/1991 | Perkins et al. | |
| 5,084,242 A | 1/1992 | Sakuma et al. | |
| 5,085,402 A | 2/1992 | O'Dell | |
| 5,085,832 A | 2/1992 | Shaw et al. | |
| 5,089,230 A | 2/1992 | Kondo et al. | |
| 5,130,095 A | 7/1992 | Ricchio et al. | |
| 5,139,743 A | 8/1992 | Ishizaka et al. | |
| 5,143,118 A | 9/1992 | Sule | |
| 5,147,608 A | 9/1992 | Hudson et al. | |
| 5,213,762 A | 5/1993 | Ricchio et al. | |
| 5,223,222 A | 6/1993 | Ricchio et al. | |
| 5,240,680 A | 8/1993 | Zuckermann et al. | |
| 5,273,715 A | 12/1993 | Bridgham et al. | |
| 5,282,978 A | 2/1994 | Polk, Jr. et al. | |
| 5,284,425 A | 2/1994 | Holtermann et al. | |
| 5,314,825 A | 5/1994 | Weyrauch et al. | |
| 5,320,139 A | 6/1994 | Paul | |
| 5,324,480 A | 6/1994 | Shumate et al. | |
| 5,332,549 A | 7/1994 | MacIndoe, Jr. | |
| 5,334,353 A | 8/1994 | Blattner | |
| 5,338,688 A | 8/1994 | Deeg et al. | |
| 5,364,068 A | 11/1994 | Farnsworth et al. | |
| 5,411,065 A | 5/1995 | Meador et al. | |
| 5,433,244 A | 7/1995 | Sule | |
| 5,509,966 A | 4/1996 | Sykes | |
| 5,518,686 A | 5/1996 | Masterson et al. | |
| 5,525,515 A | 6/1996 | Blattner | |
| 5,549,141 A | 8/1996 | Meador et al. | |
| 5,568,882 A | 10/1996 | Takacs | |
| 5,593,893 A | 1/1997 | Kobashi et al. | |
| 5,601,982 A | 2/1997 | Sargent et al. | |
| 5,624,409 A | 4/1997 | Seale | |
| 5,635,364 A | 6/1997 | Clark et al. | |
| 5,650,327 A | 7/1997 | Copeland et al. | |
| 5,697,409 A | 12/1997 | Bishop et al. | |
| 5,720,923 A | 2/1998 | Haff et al. | |
| 5,738,728 A | 4/1998 | Tisone | |
| 5,741,554 A | 4/1998 | Tisone | |
| 5,743,960 A | 4/1998 | Tisone | |
| 5,756,050 A | 5/1998 | Ershow et al. | |
| 5,762,873 A | 6/1998 | Fanning et al. | |
| 5,763,278 A | 6/1998 | Sickinger et al. | |
| 5,770,151 A | 6/1998 | Roach et al. | |
| 5,770,160 A | 6/1998 | Smith et al. | |
| 5,795,784 A | 8/1998 | Arnquist et al. | |
| 5,819,799 A | 10/1998 | O'Dell | |
| 5,827,480 A | 10/1998 | Haff et al. | |
| 5,856,193 A | 1/1999 | Fanning et al. | |
| 5,856,194 A | 1/1999 | Arnquist et al. | |
| 5,875,967 A | 3/1999 | Ruth, III | |
| 5,876,668 A | 3/1999 | Kawashima et al. | |
| 5,882,903 A | 3/1999 | Andrevski et al. | |
| 5,897,837 A | 4/1999 | Mizuno | |
| 5,916,524 A | 6/1999 | Tisone | |
| 5,921,951 A | 7/1999 | Morris | |
| 5,925,732 A | 7/1999 | Ecker et al. | |
| 5,928,131 A | 7/1999 | Prem | |
| 5,948,360 A | 9/1999 | Rao et al. | |
| 5,985,214 A | 11/1999 | Stylli et al. | |
| 5,993,627 A | 11/1999 | Anderson et al. | |
| 6,045,759 A | 4/2000 | Ford et al. | |
| 6,063,339 A | 5/2000 | Tisone et al. | |
| 6,086,824 A | 7/2000 | Fanning et al. | |
| 6,096,561 A | 8/2000 | Tayi | |
| 6,102,068 A | 8/2000 | Higdon et al. | |
| 6,143,252 A | 11/2000 | Haxo, Jr. et al. | |
| 6,197,255 B1 | 3/2001 | Miyake et al. | |
| 6,202,687 B1 | 3/2001 | Park | |
| 6,245,297 B1 | 6/2001 | Kowallis | |
| 6,306,594 B1 | 10/2001 | Cozzette et al. | |
| 6,352,861 B1 | 3/2002 | Copeland et al. | |
| 6,355,487 B1 | 3/2002 | Kowallis | |
| 6,360,794 B1 | 3/2002 | Turner | |
| 6,372,185 B1 | 4/2002 | Shumate et al. | |
| 6,387,330 B1 | 5/2002 | Bova et al. | |
| 6,395,232 B1 | 5/2002 | McBride | |
| 6,416,294 B1 | 7/2002 | Zengerle et al. | |
| 6,416,713 B1 | 7/2002 | Ford et al. | |
| 6,420,186 B1 | 7/2002 | Berger et al. | |
| 6,429,016 B1 | 8/2002 | McNeil | |
| 6,431,212 B1 | 8/2002 | Hayenga et al. | |
| 6,432,719 B1 | 8/2002 | Vann et al. | |
| 6,448,090 B1 | 9/2002 | McBride | |
| 6,468,800 B1 | 10/2002 | Stylli et al. | |
| 6,471,089 B1 | 10/2002 | Liff et al. | |
| 6,472,218 B1 | 10/2002 | Stylli et al. | |
| 2001/0023826 A1 | 9/2001 | Anderson et al. | |
| 2001/0036424 A1 | 11/2001 | Takahashi et al. | |
| 2001/0053337 A1 | 12/2001 | Doktycz et al. | |
| 2002/0001675 A1 | 1/2002 | Tisone | |
| 2002/0012611 A1 | 1/2002 | Stylli et al. | |
| 2002/0041829 A1 | 4/2002 | Kowallis | |
| 2002/0066812 A1 | 6/2002 | Gazeau | |
| 2002/0090738 A1 | 7/2002 | Cozzette et al. | |
| 2002/0110493 A1 | 8/2002 | Dales et al. | |
| 2002/0114740 A1 | 8/2002 | Yamamoto | |
| 2002/0142483 A1 | 10/2002 | Xoa | |
| 2002/0146347 A1 | 10/2002 | McNeil | |
| 2002/0151076 A1 | 10/2002 | Anderson et al. | |
| 2002/0153055 A1 | 10/2002 | Downs et al. | |
| 2002/0154799 A1 | 10/2002 | Anderson et al. | |
| 2002/0159919 A1 | 10/2002 | Churchill et al. | |
| 2002/0175078 A1 | 11/2002 | Anderson et al. | |
| 2002/0176801 A1 | 11/2002 | Giebeler et al. | |
| 2002/0176803 A1 | 11/2002 | Hamel et al. | |

FOREIGN PATENT DOCUMENTS

| | | | |
|---|---|---|---|
| EP | 0350175 A1 | 1/1990 | |
| EP | 0499477 A2 | 8/1992 | |
| EP | 1099483 A1 | 5/2001 | |
| EP | 1197693 A2 | 4/2002 | |
| WO | WO9613293 A1 | 5/1996 | |
| WO | WO9852047 A1 | 11/1998 | |
| WO | WO9934931 A1 | 7/1999 | |
| WO | WO9942752 A1 | 8/1999 | |
| WO | WO9942804 A2 | 8/1999 | |
| WO | WO0001798 A2 | 1/2000 | |
| WO | WO0045957 A1 | 8/2000 | |
| WO | WO0157254 A2 | 8/2001 | |
| WO | WO0189695 A2 | 11/2001 | |
| WO | WO0194027 A2 | 12/2001 | |
| WO | WO0203849 A2 | 1/2002 | |
| WO | WO0218053 A1 | 3/2002 | |
| WO | WO02080822 A2 | 10/2002 | |

* cited by examiner

METHOD AND APPARATUS FOR HANDLING SMALL VOLUME FLUID SAMPLES

BACKGROUND OF INVENTION

1. Field of Invention

This invention relates to handling small volume fluid samples, such as nanoliter-size fluid samples.

2. Related Art

The ability to handle small volume fluid samples, such as samples in the nanoliter-size range, can be important in biotechnology-related research, such as genomics and proteomics. Small volume sample handling is also used in other pharmaceutical or material science research, such as for drug discovery, live cell dispensing, combinatorial chemistry or other applications.

Systems that perform such sample handling are frequently used to pick up, or aspirate, samples from a work surface, such as wells in a microtiter tray. Microtiter trays are well known in the art, and commonly have 96, 384 or other numbers of wells to hold individual liquid samples. Sample handling systems also are used to place, or dispense, liquid samples in desired positions on a work surface.

SUMMARY OF INVENTION

In one aspect of the invention, a method and apparatus for aspirating and dispensing small-volume liquid samples is provided.

In one illustrative embodiment, a system for handling fluid samples includes a fluid reservoir having a diaphragm separating a liquid portion of the reservoir from a gas portion of the reservoir. A conduit fluidly couples the liquid portion of the reservoir to the input of a solenoid valve adapted open and close a passage between the input and an output of the valve. A sample handling channel is in fluid communication with the output of the solenoid valve so that a pressure in the gas portion of the reservoir controls the sample handling channel to aspirate and dispense a fluid sample in response to opening of the passage in the solenoid valve.

In one aspect of the invention, a variable pressure supply provides a controlled gas pressure in the gas portion of the reservoir. The variable pressure supply may include a servo-controlled regulator that controls a gas pressure in the gas portion of the reservoir, a vacuum source that provides a gas pressure below an ambient pressure, and/or a gas supply that provides a gas pressure above an ambient pressure.

In one aspect of the invention, a controller may control the operation of the solenoid valve to open and close the passage and control the gas pressure in the gas portion of the reservoir.

In one aspect of the invention, the sample handling channel and the solenoid valve are constructed and arranged to aspirate and dispense nanoliter-sized liquid samples.

In one aspect of the invention, a plurality of sample handling channels are each associated with a corresponding solenoid valve in fluid communication with the liquid portion of the reservoir. The sample handling channels may be arranged in a pattern to cooperate with wells in a microtiter tray, or other work surface.

In one aspect of the invention, a robotic device may move the sample handling channels relative to a work surface so liquid samples are aspirated and dispensed in desired locations.

In one aspect of the invention, the diaphragm may include a sheet of elastomeric material.

In another illustrative embodiment, a system for handling fluid samples includes a fluid supply, a variable pressure supply constructed and arranged to provide a negative pressure and a positive pressure relative to an ambient pressure, and a chamber having a flexible diaphragm separating first and second portions in the chamber. The first portion may be in fluid communication with the fluid supply and the second portion may be in communication with the variable pressure supply. A valve may be in fluid communication with the first portion of the chamber, and a needle may be in fluid communication with the valve. When a negative pressure is present in the second portion, the needle may be caused to aspirate a fluid sample when the valve is open, and when a positive pressure is present in the second portion, the needle may be caused to dispense a fluid sample when the valve is open.

In another illustrative embodiment, a method of handling liquid samples using a robotically-manipulated tool includes fluidly coupling a sample handling channel with a first end of a conduit having a valve controllable to open and close a fluid flow passage along the conduit. A second end of the conduit is fluidly coupled to a liquid portion of a reservoir, where the liquid portion of the reservoir is separated from a gas portion of the reservoir. A pressure in the gas portion of the reservoir is adjusted so liquid in the liquid portion of the reservoir is urged to flow into the conduit, and the valve is opened so that a fluid sample is dispensed from the sample handling channel. A pressure in the gas portion of the reservoir may also be adjusted so liquid in the conduit is urged to flow into the liquid portion of the reservoir, and the valve may be opened so that a fluid sample is aspirated by the sample handling channel.

In another illustrative embodiment, a method of handling liquid samples using a robotically-manipulated tool includes raising a gas pressure in a reservoir so that fluid contained in the reservoir is urged to move out of the reservoir and into a conduit connected to the reservoir. A valve that controls flow through the conduit may be opened, and a fluid sample may be dispensed from a sample handling channel fluidly coupled to the conduit. A gas pressure in the reservoir may be lowered so that fluid contained in the conduit connected to the reservoir is urged to move into the reservoir. A valve that controls flow through the conduit may be opened and a fluid sample may be aspirated into the sample handling channel.

These and other aspects of the invention will be apparent and/or obvious from the following detailed description of illustrative embodiments.

BRIEF DESCRIPTION OF DRAWINGS

Illustrative embodiments in accordance with the invention are described below with reference to the following drawings, in which like numerals reference like elements, and wherein.

In one aspect of the invention, a sample handling method and apparatus may aspirate and dispense fluid samples using a variable fluid pressure. In one illustrative embodiment, a chamber may have two portions separated by a flexible membrane or diaphragm. A first portion of the chamber may be in fluid communication with a control valve, such as a solenoid-actuated valve. A second portion of the chamber may be in communication with a variable pressure supply capable of varying the pressure in the second portion between a negative pressure and a positive pressure relative to ambient. By controlling the pressure in the second portion of the chamber, fluid in the first portion of the chamber may be caused to flow in a desired direction through the control valve. For example, if the pressure in the second portion of the chamber is adjusted to be below ambient, fluid may be drawn in a direction away from the control valve toward the first portion of the chamber. Alternately, if the pressure in the second portion of the chamber is adjusted to be above ambient, fluid in the first portion may be caused to flow toward the control valve. This arrangement can provide for highly controlled flow through the control valve since the driving pressure behind fluid in the first portion of the chamber can be very accurately controlled. This is in contrast to other systems, such as those that use movable pistons to force fluid to flow from a chamber to or from a control valve. In such systems, the pressure used to drive the fluid flow may not be accurately known or controlled. For example, a small movement of a metering piston in a liquid-filled chamber may drastically change the pressure in the chamber since the liquid may be incompressible. As a result, the driving pressure urging the liquid to exit the chamber may vary widely during operation, potentially causing variations in the volume flow rate through the control valve.

Figure 1:
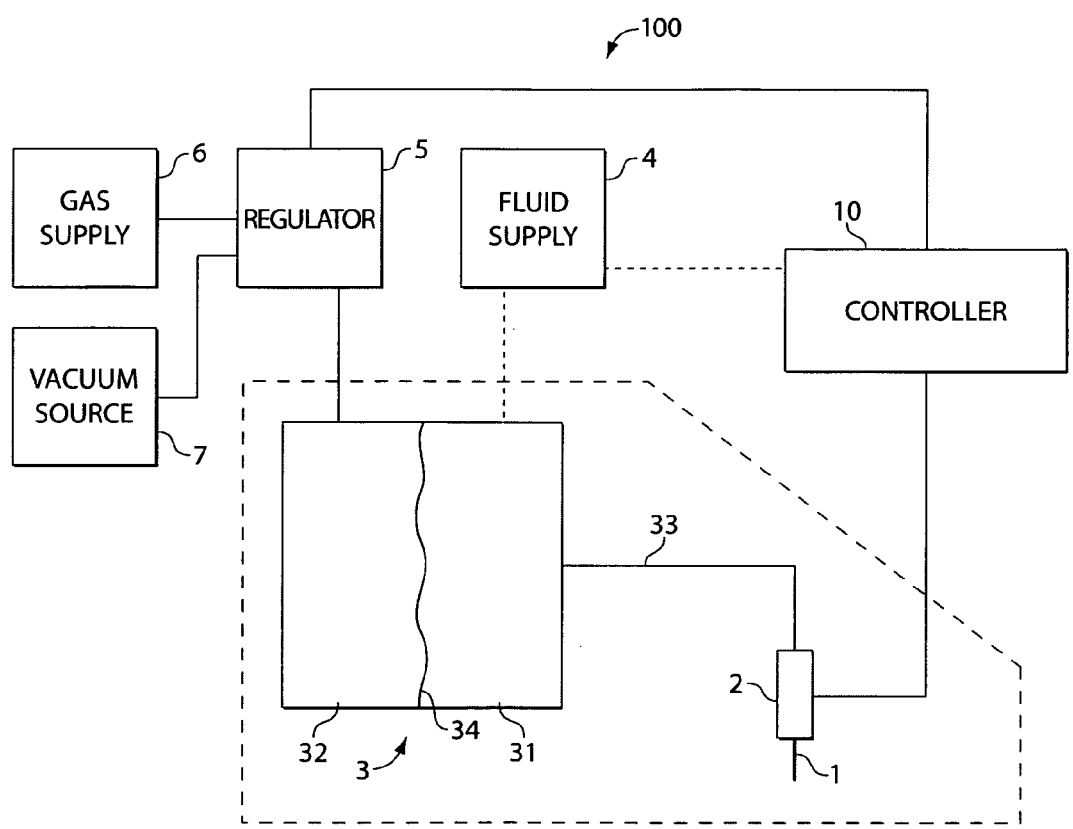
FIG. 1 is a schematic diagram of a sample handling apparatus in accordance with the invention.

FIG. 1 is a schematic block diagram of a liquid sample handling apparatus 100 in accordance with the invention. In this illustrative embodiment, one or more needles 1 may pick or place liquid samples on one or more work areas, such as wells in a microtiter tray, a gel containing separated DNA fragments or other biologic materials, etc. Any suitable sample type may be handled by the needle 1, including regents, DNA fragments, proteins, biologic cells, etc.

Control of fluid flow at the needle 1 is performed, at least in part, using a valve 2 that is fluidly coupled to a chamber 3 via a conduit 33. The chamber 3 may have a first portion 31 separated from a second portion 32 by a diaphragm 34. The diaphragm 34 may include a flexible member, such as a sheet of elastomeric material. Alternately, the diaphragm 34 may be any suitable material or device that transmits pressure between the first and second portions 31 and 32. In one embodiment, the diaphragm 34 is arranged so that a gas pressure in the second portion 32 is transferred to the first portion 31 so the pressures in both portions are balanced, e.g., equal to each other.

The first portion 31 may be filled with liquid from a fluid supply 4, such as a fluid tank or other reservoir. The liquid may completely fill the first portion 31 as well as the conduit 33 up to the valve 2. The liquid in the first portion 31 may be any suitable liquid, such as distilled water, a liquid reagent or other material.

The second portion 32 may be entirely filled with a gas, such as air. The gas may be provided to the second portion 32 via a variable pressure supply that can adjust the pressure in the second portion 32 as desired. The variable pressure supply in this embodiment includes a regulator 5 that may control the pressure of the gas in the second portion 32. In one embodiment, the regulator 5 is a servo-controlled regulator that uses feedback, e.g., from a pressure sensor, to maintain a desired pressure in the first and/or second portion 31, 32 under the control of the controller 10. The variable pressure supply may also include a gas supply 6 and/or a vacuum source 7 coupled with the regulator 5 and/or the second portion 32 to help adjust the pressure in the second portion 32. For example, if a pressure is to be raised in the second portion 32, gas from the gas supply 6 may be provided to the second portion 32 until the desired pressure is obtained. Conversely, if a pressure in the second portion 32 is to be lowered, the second portion 32 may be coupled to the vacuum source 7 so gas is removed from the second portion 32 and the pressure is suitably decreased. The gas supply 6 and the vacuum source 7 may include any suitable components to provide a pressure source or a vacuum source. For example, the gas supply 6 may include a compressor, pump, tank of compressed gas or other. The vacuum source 7 may include a vacuum pump, a venturi-type vacuum device, or other suitable arrangement. The regulator 5 may also take any suitable form so that the pressure in the second portion 32 may be accurately controlled.

The valve 2, fluid supply 4, regulator 5 and any other suitable portions of the sample handling apparatus 100 may be controlled by a controller 10. That is, the controller 10 may output and receive signals with respect to components in the system 100 so that the system 100 operates as desired to aspirate and dispense samples. The controller 10 may send and receive signals in any suitable way, such as by wired and/or wireless link, and in any suitable format and/or communications protocol. The controller 10 may include any suitable general purpose data processing system, which can be, or include a suitably programmed general purpose computer, or network of general purpose computers and other associated devices. Such associated devices may include communication devices and/or other circuitry or components necessary to perform the desired input/output or other functions. The controller 10 may also be implemented at least in part as single special purpose integrated circuits (e.g. ASICs), or an array of ASICs, each having a main or central processor section for overall, system-level control and separate sections dedicated to performing various different specific computations, functions and other processes under the control of the central processor section. The controller may also be implemented using a plurality of separate dedicated programmable integrated or other electronic circuits or devices, e.g., hard wired electronic or logic circuits, such as discrete element circuits or programmable logic devices. The controller may also include other devices, such as information display devices, user input devices such as a keyboard, user pointing device, touch screen or other interface, data storage devices or other electronic circuitry or components. The controller 10 may be part of a robot control system that includes a robot arm or other device to move portions of the sample handling system 100 so samples are picked and placed in desired locations. The robotic control system may include a machine vision system to help direct the positioning of portions of the device, as is well known in the art.

To aspirate a liquid sample the needle 1, the controller 10 may instruct the regulator 5 to adjust the pressure in the second portion 32 so that it is suitably below an ambient pressure. For example, the regulator 5 may fluidly couple the second portion 32 to the vacuum source 7 so that a suitably low pressure is established in the second portion 32. The relatively low pressure in the second portion 32 may cause the diaphragm 34 to be generally urged toward the left in FIG. 1 so the pressure drops in the first portion 31. Thus, when the controller 10 causes the valve 2 to open, liquid may be withdrawn from the conduit 33 into the first portion 31. As a result, a liquid sample at the needle 1 may be withdrawn, or aspirated, into the needle 1 from a work surface. Close control of the pressure in the second portion 32 and/or a time that the valve 2 is effectively opened may allow for precise control of the volume of the sample that is aspirated by the needle 1. In some circumstances, a gas or air bubble may separate the liquid sample aspirated into the needle 1 from the control liquid in the conduit 33 and the first portion 31. For example, liquid from the first portion 31 and conduit 33 may fill a passage through the valve 2 and extend somewhat past the valve 2 towards the needle 1. A gas bubble may separate the liquid from a sample in the needle 1. Providing such separation may prevent the sample from contaminating the control liquid in the first portion 31 and/or vice versa.

To dispense a sample from the needle 1, the regulator 5 may adjust the pressure in the second portion 32 so it is suitable above an ambient pressure. For example, the regulator 5 may fluidly couple the second portion 32 to a gas supply 6 until a desired pressure in the second portion 32 is obtained. A relatively high pressure in the second portion 32 may urge the diaphragm 34 to move generally toward the right increasing pressure in the first portion 31 and in the conduit 33. As a result, when the valve 2 is opened, fluid may move from the first portion 31 into the conduit 33 and therefore cause a liquid sample in the needle 1 to be dispensed onto a work surface. The sample dispensed from the needle 1 may be a previously aspirated sample, or a liquid, such as a reagent, in the first portion 31 and the conduit 33 may be dispensed in precise volumes from the needle 1.

Precise control of the volume of samples aspirated or dispensed may be controlled based on the pressure established in the second portion 32 and/or the timing that the valve 2 is opened. The valve 2 opening/closing timing may be controlled by applying a pulsed electrical signal to a solenoid actuator in the valve so the valve is opened and closed at a high frequency, such as 10 Hz or higher. By rapidly opening and closing the valve, the amount of liquid allowed to pass the valve may be precisely controlled. For example, the controller 10 may store information that represents an amount of liquid that is passed through the valve for each open/close cycle for a given pressure in the second portion 32. To aspirate/dispense a sample of a desired volume, the controller may divide the desired sample volume by the volume passed per cycle by the valve to give a total number of cycles that the valve should be opened/closed. The controller may then provide the valve with a suitable signal to cause the valve to open/close for the total number of cycles for each dispense/aspirate operation. It will be understood that this is only one example of how volume control may be performed in an illustrative embodiment. The controller may use any suitable process to perform desired volume control for samples.

Figure 2:
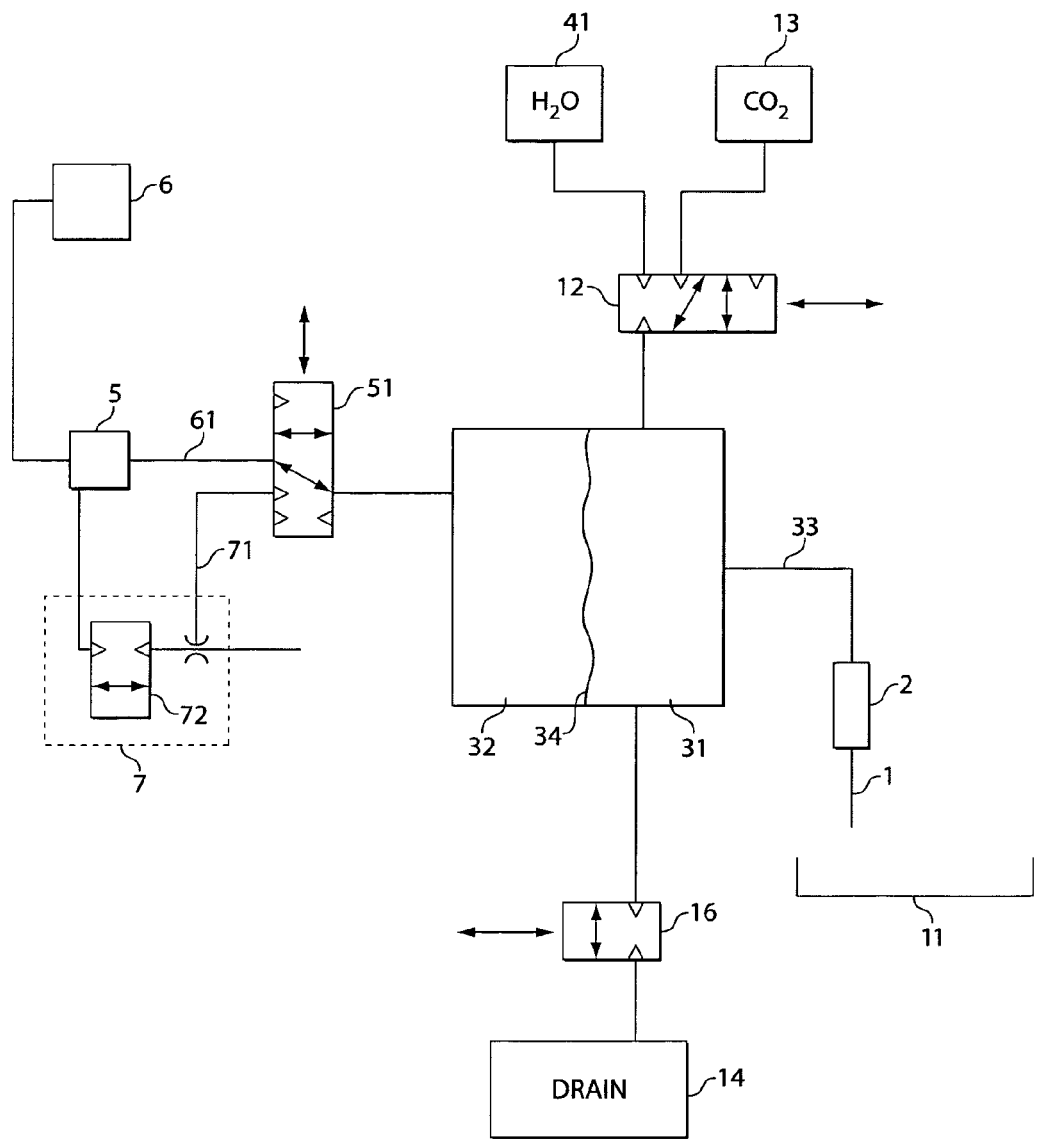
FIG. 2 is a more detailed schematic diagram of a sample handling apparatus in accordance with the invention.

FIG. 2 is a schematic block diagram of the system 100 in a somewhat more detailed form than that shown in FIG. 1. In this illustrative embodiment, the system 100 may be prepared for use in handling liquid samples by first removing all fluid from the first portion 31, the conduit 33, valve 2 and needle 1. To evacuate these portions of the system, a valve 12 may be adjusted to fluidly couple a gas source, such as a source of pressurized carbon dioxide gas 13, to the first portion 31. A valve 16 may also be opened so that fluid in the first portion 31 may exit through the valve 16 to a drain 14. The valve 2 may also be opened so that pressurized gas forces fluid to exit the conduit 33, valve 2 and needle 1 into a rinsing reservoir or other container 11. Once the system has been evacuated, the first portion 31 may be rinsed with fluid from a fluid supply, such as a source of distilled water 41. The valve 12 may couple the source of distilled water 41 to the first portion 31 so the first portion 31 is filled with liquid.

The valve 2 may also be opened so that the conduit 33 and needle 1 may be rinsed with the distilled water or other suitable liquid.

Once the rinsing operation is complete, the valves 12, 16 and 2 may be closed and the system may be used for sample handling. For example, if distilled water, a reagent, or other fluid in the first portion 31 is to be dispensed from the needle 1, a valve 51 may couple a gas supply line 61 from the regulator 5 to the second portion 32. This may create a suitable pressure in the second portion 31 so that liquid in the first portion 31 is forced to flow into the conduit 33 and out of the needle 1 when the valve 2 is opened. Alternately, the valve 51 may couple a vacuum supply line 71 to the second portion 32. The vacuum may be created in any suitable way, however in this illustrative embodiment, the vacuum source 7 includes a valve 72 that when opened allows a gas under pressure to flow through a venturi-like element that creates a vacuum in line 71. Creation of a suitably low pressure in the second portion 32 may cause fluid to be withdrawn from the conduit 33 and into the needle 1 from a work surface when the valve 2 is opened. As will be understood, liquid samples aspirated at the needle 1 may be dispensed by suitably raising the pressure in the second portion 32 so the sample is dispensed from the needle 1 when the valve 2 is opened.

Although in the illustrative embodiments shown above, the chamber 3 is coupled to only 1 conduit 33 and valve 2, any suitable number of conduits 33, valves 2 and/or needles 1 may be fluidly coupled to the chamber 3. For example, several conduits 33 may be coupled to the first portion 31 and each lead to a corresponding valve to and needle 1. As a result, by controlling each of the valves to open and close, fluid flow for each of several needles 1 can be controlled. This arrangement can allow a sample handling device to individually aspirate or dispense samples at specific needles and/or simultaneously aspirate or dispense samples from several needles 1.

The valves 2 may be any suitable electrically-control valve or other. In one illustrative embodiment, the valves 2 may be solenoid valves capable of dispensing approximately 10 nanoliter or larger size samples offered by The Lee Company of Westbrook, Conn. Such valves may be opened and closed at high frequencies, e.g., up to 1200 Hz, based on a pulsed signal provided from the controller 10. Such operation may allow for precise metering of samples aspirated and/or dispensed by a needle coupled to the valve. The needles may also be of any suitable type and/or size. In one embodiment, the needles may include jeweled tubes or other channels in which a sapphire or other similar material lines the interior of a stainless steel tube. The needles may alternately receive replaceable tips, e.g., made of plastic.

While the invention as been described with reference to various illustrative embodiments, the invention is not limited to embodiments described. Thus, it is evident that many alternatives, modifications, and variations of the embodiments described will be apparent to those skilled in the art. Accordingly, embodiments of the invention as set forth herein are intended to be illustrative, not limiting. Various changes may be made without departing from the invention.

What is claimed is:

1. A system for handling fluid samples comprising:
a fluid reservoir having a diaphragm separating a liquid portion of the reservoir from a gas portion of the reservoir;
a variable pressure supply that includes a servo-controlled regulator to provide a controlled gas pressure in the gas portion of the reservoir;

a solenoid valve having an input and an output, the solenoid valve adapted to open and close a passage between the input and the output;

a conduit fluidly coupling the liquid portion of the reservoir to the input of the solenoid valve; and a sample handling channel in fluid communication with the output of the solenoid valve;

wherein a pressure in the gas portion of the reservoir controls the sample handling channel to aspirate and dispense a fluid sample in response to opening of the passage in the solenoid valve.

2. The system of claim 1, wherein the variable pressure supply includes a vacuum source that provides a gas pressure below an ambient pressure and a gas supply that provides a gas pressure above an ambient pressure.

3. The system of claim 1, further comprising:

a controller that controls operation of the solenoid valve to open and close the passage and controls the gas pressure in the gas portion of the reservoir.

4. The system of claim 3, wherein the solenoid valve is controlled to open and close at a high frequency.

5. The system of claim 1, wherein the sample handling channel and the solenoid valve are constructed and arranged to aspirate and dispense nanoliter-sized liquid samples.

6. The system of claim 1, wherein the sample handling channel includes a jeweled needle.

7. The system of claim 1, further comprising:

a plurality of sample handling channels each associated with a corresponding solenoid valve in fluid communication with the liquid portion of the reservoir, the sample handling channels arranged in a pattern to cooperate with wells in a microtiter tray.

8. The system of claim 7, further comprising:

a robotic device that moves the sample handling channels relative to a work surface so liquid samples are aspirated and dispensed in desired locations.

9. The system of claim 1, wherein the diaphragm includes a sheet of elastomeric material.

10. A liquid sample handling apparatus comprising:

a fluid supply;

a variable pressure supply constructed and arranged to provide a negative pressure and a positive pressure relative to an ambient pressure;

a chamber having a flexible diaphragm separating first and second portions in the chamber, the first portion being in fluid communication with the fluid supply and the second portion being in communication with the variable pressure supply;

a valve in fluid communication with the first portion of the chamber; and a needle in fluid communication with the valve;

wherein the variable pressure supply includes a servo-controlled regulator that controls a gas pressure in the second portion of the chamber, and wherein a negative pressure in the second portion causes the needle to aspirate a fluid sample when the valve is open, and a positive pressure in the second portion causes the needle to dispense a fluid sample when the valve is open.

11. The apparatus of claim 10, wherein the variable pressure supply includes a vacuum source that provides a gas pressure below an ambient pressure and a gas supply that provides a gas pressure above an ambient pressure.

12. The apparatus of claim 10, further comprising:

a controller that controls the operation of the valve to open and close and controls the pressure in the second portion of the chamber.

13. The apparatus of claim 10, wherein the valve is a solenoid valve.

14. The apparatus of claim 10, wherein the needle and the valve are constructed and arranged to aspirate and dispense nanoliter-sized liquid samples.

15. The apparatus of claim 10, further comprising:

a plurality of needles each associated with a corresponding valve in fluid communication with the first portion of the chamber, the needles arranged in a pattern to cooperate with wells in a microtiter tray.

16. The apparatus of claim 15, further comprising:

a robotic device that moves the needles relative to a work surface so liquid samples are aspirated and dispensed in desired locations.

17. The apparatus of claim 10, wherein the flexible diaphragm includes a sheet of elastomeric material.

18. A method of handling liquid samples using a robotically-manipulated tool, the method comprising:

fluidly coupling a sample handling channel with a first end of a conduit having a valve controllable to open and close a fluid flow passage along the conduit;

fluidly coupling a second end of the conduit opposite the first end to a liquid portion of a reservoir, the liquid portion of the reservoir being separated from a gas portion of the reservoir;

adjusting a pressure in the gas portion of the reservoir so liquid in the liquid portion of the reservoir is urged to flow into the conduit and opening the valve so that a fluid sample is dispensed from the sample handling channel; and adjusting a pressure in the gas portion of the reservoir so liquid in the conduit is urged to flow into the liquid portion of the reservoir and opening the valve so that a fluid sample is aspirated by the sample handling channel;

wherein the steps of adjusting a pressure include using a servo-controlled regulator to control pressure in the gas portion of the reservoir.

19. A method of handling liquid samples using a robotically-manipulated tool, the method comprising:

raising a gas pressure in a reservoir using a servo-controlled regulator so that fluid contained in the reservoir is urged to move out of the reservoir and into a conduit connected to the reservoir;

opening a valve that controls flow through the conduit;

dispensing a fluid sample from a sample handling channel fluidly coupled to the conduit;

lowering a gas pressure in the reservoir using a servo-controlled regulator so that fluid contained in the conduit connected to the reservoir is urged to move into the reservoir;

opening a valve that controls flow through the conduit; and aspirating a fluid sample into the sample handling channel.

20. An apparatus for handling liquid samples using a robotically-manipulated tool, the apparatus comprising:

means for fluidly coupling a sample handling channel with a first end of a conduit having a valve controllable to open and close a fluid flow passage along the conduit;

means for fluidly coupling a second end of the conduit opposite the first end to a liquid portion of a reservoir, the liquid portion of the reservoir being separated from a gas portion of the reservoir;

means for adjusting a pressure in the gas portion of the reservoir so liquid in the liquid portion of the reservoir is urged to flow into the conduit and opening the valve so that a fluid sample is dispensed from the sample handling channel; and means for adjusting a pressure in the gas portion of the reservoir so liquid in the conduit is urged to flow into the liquid portion of the reservoir and opening the valve so that a fluid sample is aspirated by the sample handling channel;

wherein the means for adjusting includes a servo-controlled regulator to control pressure in the gas portion of the reservoir.

21. A system for handling fluid samples comprising:

a fluid reservoir having a diaphragm separating a liquid portion of the reservoir from a gas portion of the reservoir;

a solenoid valve having an input and an output, the solenoid valve adapted to open and close a passage between the input and the output;

a conduit fluidly coupling the liquid portion of the reservoir to the input of the solenoid valve; and a sample handling channel having a jeweled needle in fluid communication with the output of the solenoid valve;

wherein a pressure in the gas portion of the reservoir controls the sample handling channel to aspirate and dispense a fluid sample in response to opening of the passage in the solenoid valve.

* * * * *